United States Patent [19]

Mast

[11] 4,296,628
[45] Oct. 27, 1981

[54] SYSTEM FOR DETECTING PARTICLES CARRIED BY A FLUID FLOW

[75] Inventor: Harm Mast, Rijswijk, Netherlands

[73] Assignee: Shell Oil Company, Houston, Tex.

[21] Appl. No.: 156,847

[22] Filed: Jun. 5, 1980

[30] Foreign Application Priority Data

Jun. 26, 1979 [GB] United Kingdom ............... 22277/79

[51] Int. Cl.³ ............................................ G01N 15/07
[52] U.S. Cl. ....................................... 73/28; 73/61 R
[58] Field of Search .................. 73/61 R, 592, 861.18, 73/861.21, 28; 340/310, 327

[56] References Cited

U.S. PATENT DOCUMENTS

| | | |
|---|---|---|
| 2,760,184 | 8/1956 | Beattie . |
| 3,271,672 | 9/1966 | Henderson . |
| 3,563,311 | 2/1971 | Stein . |
| 3,816,773 | 6/1974 | Baldwin . |
| 3,834,227 | 9/1974 | Patterson . |
| 3,841,144 | 10/1974 | Baldwin . |
| 3,844,174 | 10/1974 | Chabre . |
| 3,854,323 | 12/1974 | Hearn et al. . |
| 3,908,454 | 9/1975 | Mullins . |
| 3,989,965 | 11/1976 | Smith . |
| 4,016,766 | 4/1977 | Morris . |
| 4,065,960 | 1/1978 | Grabendorfer . |

OTHER PUBLICATIONS

Vriezen et al., Sand Detection in Production Lines, Society of Petroleum Engineers of AIME, Paper SPE No. 4825, 1974.

Primary Examiner—S. Clement Swisher

[57] ABSTRACT

A sensor system for detecting sand in a gas/liquid flow passing through a pipeline comprising two sensors located in the flow. One of the sensors is covered with a layer of acoustic dampening material. By subtracting the signals generated by the sensors, a signal is obtained that is substantially free from noise generated by the gas present in the two phase flow.

6 Claims, 1 Drawing Figure

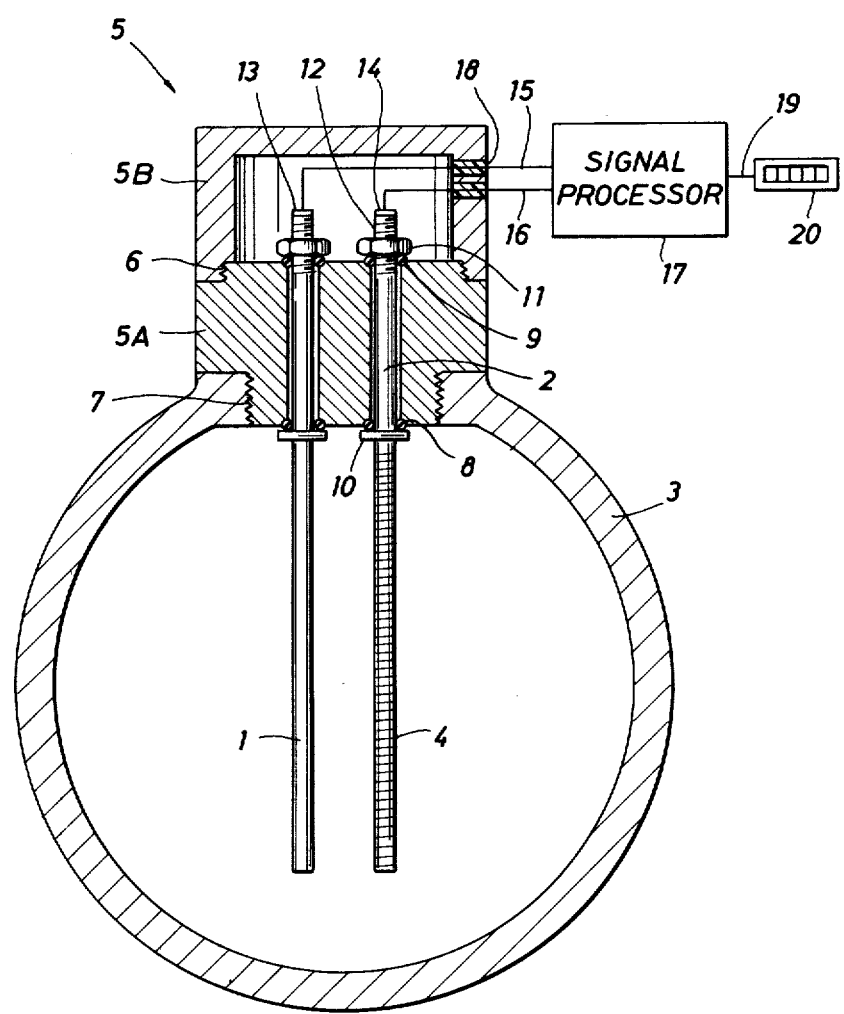

SYSTEM FOR DETECTING PARTICLES CARRIED BY A FLUID FLOW

BACKGROUND OF THE INVENTION

The invention relates to a system for detecting particles carried by a fluid flow. Detection of particles in a fluid flowing through a conduit is often desirable, in particular when monitoring flows of well fluids such as water and/or oil and/or gas being produced from underground permeable formation layers that are penetrated by wells extending from the surface of the earth into the said layers.

The fluids passing out of the formation layers into the wells are transported through the wells to the surface. Often, these fluids carry solid particles such as sand grains that are dragged from the formation layers by the flowing fluid. These particles will damage the production equipment, such as by erosive action, or settle down in parts of the equipment, thereby necessitating frequent cleaning of the equipment. To prevent this, the fluid flow should be monitored in order to allow the operator to take the necessary steps when unallowable amounts of sand grains are found to be present in the fluid flow.

To monitor the fluid flow carrying particles therewith, use has been made of systems including a metal rod that is exposed to the flow of fluid. The particles on impinging against the rod, generate acoustic energy, which energy is detected by an acoustical transducer means (such as a piezo-electric element) cooperating with the rod. The transducer means generates electric signals that are representative of the acoustic energy generated by the particles that have contacted the rod. By gauging or calibrating the system, reference data can be obtained that are representative for the total amount and/or mass of particles that is present in the flow.

It has been found that although the measuring results obtainable by the above systems are reliable in single-phase flow, problems arise when applying the systems in multi-phase flow, such as in a two-phase flow, in particular when the two phases are a gas and a liquid.

BRIEF SUMMARY OF THE INVENTION

The object of the invention is to solve these problems and to improve the known systems such that reliable measuring results can be obtained thereby when the systems are applied in monitoring multi-phase (such as two-phase) fluid flow carrying particles therewith.

The system according to the invention includes at least two metal bodies, each cooperating with an acoustic transducer means adapted to detect acoustic energy in the relevant body and to generate electric signals representative of such energy, one of the bodies having at least part of the metal surface thereof covered with a layer of acoustic dampening material, and means for subtracting one of the electric signals from the other signal, and displaying and/or recording the resulting signal.

The area of the layer of acoustic dampening material and the location thereof on one of the bodies is chosen such that the layer at least covers that part of the surface of the body on which particles will impact when the body is mounted in a conduit through which a fluid flow carrying particles is passing.

Any material suitable for dampening acoustic waves may be used for the purpose. Polyvinylchloride has been found to be an attractive material. The material may be in the form of an adhesive tape that is wound in at least a single layer around the body.

BRIEF DESCRIPTION OF THE DRAWING

The system according to the invention will be described in more detail with reference to the drawing which shows schematically a cross-section of a conduit wherein metal bodies in the form of solid rods have been mounted.

PREFERRED EMBODIMENT

The rods 1 and 2 are made of stainless steel and are positioned in a plane that is perpendicular to the central axis of a cylindrical conduit 3.

The rods 1 and 2 are in the form of solid bars of circular cross-section and the outer surface of the rod 1 is bare, whereas the outer surface of the rod 2 is covered with an acoustic dampening layer 4 formed by a plurality of windings of adhesive tape made of polyvinylchloride having a thickness of about 1 mm. The outer diameter of the acoustic dampening material 4 on the rod 2 may be between 6–16 millimeters and is substantially equal to the outer diameter of the rod 1. The rods 1 and 2 are parallel to each other and the width of the fluid passage between the rod 1 and the acoustic dampening material 4 may be of the same magnitude as the diameter of the rod 1 (say 5 mm width at a diameter of 8 mm) or even smaller.

Each rod is supported by the housing 5 consisting of a bottom member 5A and a top member 5B provided with suitable threaded means 6 for interconnecting the members, and with threaded means 7 for mounting the housing 5 on the conduit 3.

To prevent acoustic coupling between the rods 1 and 2 via the material of the conduit 3, as well as to prevent acoustic energy generated in the material of the conduit 3 to be detected by the rods 1 and 2, each of the rods is supported and sealed in the housing 5 through the intermediary of rings 8 and 9 of elastic material, such as rubber. Each rod is clamped to the housing 5 by means of the ring-shaped shoulder 10 forming part of the rod, and the nut 11 cooperating with the screw thread 12 on the rod.

Piezo-electric elements 13 and 14 are glued on top of the rods 1 and 2, respectively, and double-lead electric cables 15 and 16 electrically connect the sides of the piezo-electric elements 13 and 14, respectively, to a signal processor 17 wherein the signal obtained from the piezo-electric element 14 cooperating with the rod 2 is subtracted from the signal obtained from the piezo-electric element 13 cooperating with the rod 1. Each of the cables 15 and 16 passes through a grommet 18 situated in an opening in the wall of the upper 5B of the housing 5. The signal resulting from the subtracting operation is passed via the electric cable 19 to a display device 20, wherein the resulting signal may also be recorded.

Apart from low-energy background noise, any liquid flowing through the conduit 3 does not generate a signal in any one of the transducers 13 and 14 mounted on the rods 1 and 2, respectively. By adding gas to the liquid flow, the resulting two-phase fluid flow generates a signal in the transducer 13 cooperating with the rod 1, and will therefore interfere with the signals generated in the said transducer by the impacts of sand particles if such particles should be detected in such two-phase fluid flow by means of a single rod of the type of rod 1.

Since, however, the signals generated in the two transducers 13 and 14 are found to be equal as far as they result from the presence of gas bubbles in the flow, but to differ as far as they result from the presence of sand particles, the final signal that is obtained by subtracting the signals one from another in the processor 17 will not contain any information on the presence of gas bubbles in the fluid flow, but will be representative only for the presence of sand particles in said flow.

It will be understood that other acoustic dampening materials than the one described with reference to FIG. 1 may be used. Such materials are of resilient nature as can be found among thermoplastics, elastomers and resinous materials. The best choice for a particular situation can be made by comparing the signals that are generated by the transducers 13 and 14 when covering the rod 2 with various types of materials having various thicknesses (such as in the range of 0.5 to 5 millimeters) and subjecting the rods to a two-phase fluid flow that does not carry particles.

The acoustic dampening materials may be applied in various forms other than a length of adhesive tape wound in at least one layer around the rod 2. If desired, the rod 2 may be covered with an acoustic dampening material in the form of a tube that is connected to the rod by gluing or shrinkage of the material, but other constructional forms may be applied as well for this purpose.

The rods 1 and 2 may be in supporting contact with the housing 5 in a manner other than the one shown in the drawing. If desired, a cylindrically shaped body of resilient or elastic material may be mounted in the annular space between the housing 5 and each of the rods.

The rods 1 and 2 are symmetrically arranged with respect to a plane of symmetry of the conduit in which they are situated, since the amounts of sand grains and gas bubbles that come into contact with the rods should be substantially equal for each rod. The rods, however, are not necessarily straight, but curved rods may be used as well. The best position of the rods in the conduit is chosen such that the rods are placed symmetrically with respect to the particle distribution over the cross-section of the fluid flow.

The rods 1 and 2 of the embodiment shown in the drawing are located in a vertical plane of a horizontally extending conduit. However, the invention is not restricted hereto. In an extreme situation, the rods may be arranged in a horizontal plane of such a conduit, in a manner such that the ends thereof face the fluid flow.

The shapes of the rod 1 without an acoustic dampening layer and of the rod 2 with the acoustic dampening layer 4 arranged thereon are equal to each other for the parts thereof that are in contact with the fluid flow. Thus, the cross section of rod 2 should be decreased to compensate for the thickness of the layer 4. However, the rod 2 should be sufficiently stiff to prevent bending movements when being subjected to the fluid flow, which movements might give rise to acoustic waves in the rod.

Application of the invention is not restricted to the use of rods having circular cross-section. Other shapes of cross section may be applied as well with equal good results.

If desired, the rods 1 and 2 may be hollow and be formed by metal tubes of a wall thickness that is sufficient to prevent bending of the tubes by the fluid flowing through the conduit. The bottom end of the rods may be closed off such that the interior of the hollow rods is separated from the interior of the conduit. The interiors of the rods may be filled with a liquid and the transducers may be freely suspended in the liquid-filled interior of the relevant rod instead of being located on the top end thereof.

It will be appreciated that good results may also be obtained by using a rod 2 having only the part facing the fluid flow covered with acoustic dampening material. Only if the fluid flow raises eddy currents by which the particles might impact on the non-covered parts of the rod 2 (such as thet part downstream of the fluid flow or the bottom end thereof) measures should be taken to cover also these parts by acoustic dampening material.

The signals generated by the acoustic transducers may be amplified, filtered and/or subjected to other treatments that are typical for signal transmission and recording techniques. It will be appreciated that the system should be calibrated such that the signals obtained after amplification of the electric signals generated by the two piezo-electic crystals are of equal strength when the bodies carrying the crystals are subjected to a two-phase fluid flow that does not carry particles.

The acoustic transducers may cooperate with the metal bodies in any desired manner. Piezo-electric elements are preferred, although other means may be used as well. The elements may be clamped by springs or screws onto the bodies in place of gluing.

What is claimed is:

1. A system for detecting particles carried by a fluid flow, said system including:

at least two metal bodies each cooperating with an acoustical transducer means adapted to detect acoustic energy in the relevant body and to generate electric signals representative of such energy, one of the bodies having at least part of the metal surface thereof covered with a layer of acoustic dampening material; and, means for substracting one of the electric signals from the other signal and recording the resulting signal.

2. The system according to claim 1, wherein the bodies consist of metal rods that are supported by a housing means disposed to acoustically insulate said rods from said housing, the rods at one end thereof at least partly protruding from the housing, and the housing being adapted to be mounted in the wall of a conduit.

3. The system according to claim 2, wherein the metal rods are solid rods.

4. The system according to any one of the claims 1-3, wherein the layer of acoustic dampening material consists of polyvinylchloride.

5. The system according to claim 2, including a conduit having a vertical plane of symmetry, the metal rods being supported by the wall of the conduit such that at least part of each rod extends in the interior of the conduit, the parts extending in the interior of the conduit being located in a plane substantially perpendicular to the plane of symmetry, and being symmetrically arranged with respect of said latter plane.

6. The system according to any one of the claims 1-3, wherein the outer diameter of the layer of acoustic dampening material carried by one of the bodies is substantially equal to the outer diameter of the other body.

* * * * *